| United States Patent [19] | [11] | 4,138,439 |
|---|---|---|
| Schultz et al. | [45] | Feb. 6, 1979 |

[54] METHOD OF PREPARING 1,1-DIFLUOROETHANE

[75] Inventors: Neithart Schultz, Eichsel; Hans-Joachim Vahlensieck, Wehr; Peter Martens, Rheinfelden, all of Fed. Rep. of Germany

[73] Assignee: Dynamit Nobel Aktiengesellschaft, Troisdorf, Fed. Rep. of Germany

[21] Appl. No.: 734,212

[22] Filed: Oct. 20, 1976

[30] Foreign Application Priority Data

Oct. 22, 1975 [DE] Fed. Rep. of Germany ....... 2547182

[51] Int. Cl.$^2$ ............................................. C07C 17/08
[52] U.S. Cl. .................................................. 260/653.6
[58] Field of Search ...................................... 260/653.6

[56] References Cited

U.S. PATENT DOCUMENTS

| 2,471,525 | 5/1949 | Hillyer et al. | 260/653.6 |
| 3,395,187 | 7/1968 | Christoph | 260/653.6 |
| 3,591,646 | 7/1971 | Vecchio et al. | 260/653.6 |
| 3,720,722 | 3/1973 | Wada et al. | 260/653.6 |
| 3,810,948 | 5/1974 | Meussdoerffer | 260/653.6 |
| 3,904,701 | 9/1975 | Schultz et al. | 260/653.6 |

*Primary Examiner*—O. R. Vertiz
*Assistant Examiner*—Wayne A. Langel
*Attorney, Agent, or Firm*—Sprung, Felfe, Horn, Lynch & Kramer

[57] ABSTRACT

A process for preparing 1,1-difluoroethane by contacting acetylene with hydrogen fluoride in the presence of an aluminum fluoride containing catalyst, the hydrofluorination being carried out at a temperature between 150 and 350° C. employing a residence time of one to 60 seconds. The catalyst employed is one prepared by imbibing gamma or eta aluminum oxide with a solution of a bismuth salt and a manganese salt. The so-imbibed catalyst is heated at a temperature between 150 and 250° C. initially in a nitrogen atmosphere and then, after complete drying, in a mixture of air employing increasing concentrations of hydrogen fluoride up to 100 percent hydrogen fluoride atmosphere. The finished catalyst contains:

0.1 to 20 weight percent of bismuth,
0.1 to 10 weight percent of manganese,
20 to 38 weight percent of aluminum,
32 to 60 weight percent of fluorine, the balance consisting essentially of oxygen.

3 Claims, No Drawings

METHOD OF PREPARING 1,1-DIFLUOROETHANE

BACKGROUND OF THE INVENTION

1. Field of the Invention

This invention relates to a process for the preparation of 1,1-difluoroethane by the hydrofluorination of acetylene employing a catalyst containing aluminum fluoride. More particularly this invention is directed to the hydrofluorination of acetylene employing a catalyst prepared by imbibing gamma or eta aluminum oxide with a solution of a bismuth and manganese salt, heating the so-imbibed catalyst at 150°–250° C., initially in a nitrogen atmosphere, and then following complete drying, heating the same in a mixture of air and hydrogen fluoride with increasing concentrations of hydrogen fluoride up to 100 percent hydrogen fluoride atmosphere. The catalyst is characterized by a quantity of bismuth, manganese, aluminum, fluorine and oxygen.

2. Discussion of the Prior Art

It is known to hydrofluorinate acetylene with the use of a catalyst consisting of a tableted mixture of aluminum fluoride and bismuth fluoride (Japanese Patent Application 7208/1968). The catalyst in this case is produced either by mixing the two fluorides in solid, powder or granulated form, and then tableting them, or by fluorinating a mixture of solid aluminum and bismuth compounds. It is also mentioned in this Patent Application that the aluminum compounds can be sintered and the tablets thus produced can be surface coated with the bismuth salts by immersion in a bismuth salt solution. A catalyst prepared in this manner, however, must still be applied to a suitable catalyst support before it is subjected to the hydrofluoric acid treatment.

With a catalyst produced in this manner one obtains 70 to 72 weight percent of 1,1-difluorethane and 25 to 27 weight percent of vinyl fluoride, with a maximum transformation of 97 percent of the acetylene charged.

These yields of 1,1-difluoroethane, however, are too small if it is desired to obtain this compound as the main product and use it for the preparation of vinylidene fluoride, for example. The use of a catalyst made in this manner also entails the disadvantage that it can be regenerated only poorly.

Through German Offenlegungsschrift 2,000,200 it is furthermore known to hydrofluorinate halogenated hydrocarbons with a catalyst containing aluminum fluoride. The catalyst used in this manner is prepared by imbibing gamma or eta aluminum oxide with a bismuth and manganese salt solution, drying the salt-impregnated aluminum oxide at temperatures up to 100° C., and then heating, first in a nitrogen atmosphere, and later in air, with increasing concentrations of hydrogen fluoride up to a 100% hydrogen fluoride atmosphere, at temperatures between 150° and 250° C.

The compounds which have hitherto been hydrofluorinated with this catalyst comprise only halogenated hydrocarbons. Furthermore, these hydrocarbons are either saturated or they contain an olefinic double bond. The hydrofluorination of these compounds is performed at temperatures between 120° and 400° C., preferably 150° to 250° C.; the detention time is between 0.1 and 40 seconds.

SUMMARY OF THE INVENTION

In accordance with the present invention, it has been found that non-halogenated hydrocarbons containing a triple bond can be hydrofluorinated with the catalyst described in said German Offenlegungsschrift 2,000,200 whereby to prepare 1,1-difluoroethane. Accordingly the present invention contemplates a process for preparing 1,1-difluoroethane by contacting acetylene with hydrogen fluoride in the presence of a catalyst containing aluminum fluoride, said hydrofluorination being carried out at a temperature between 150° and 250° C. employing a residence time of 1 to 60 seconds.

The catalyst employed in accordance with the claimed process is one prepared by imbibing gamma or eta aluminum oxide with a solution of a bismuth salt and a manganese salt, thereafter heating the same at a temperature between 150° and 250° C., initially in a nitrogen atmosphere and then, following drying, with a mixture of air and hydrogen fluoride, the concentration of air and hydrogen fluoride being changed with increasing quantities of hydrogen fluoride up to a 100 percent hydrogen fluoride atmosphere. The resultant catalyst consists essentially of:

0.1 to 20 weight percent bismuth,
0.1 to 10 weight percent manganese,
20 to 38 weight percent aluminum,
32 to 60 weight percent fluorine, the balance consisting essentially of oxygen.

By the use of this methods, yields are obtained of 96 to 98 percent of the desired 1,1-difluoroethane, the transformation of the acetylene being virtually complete. This high transformation of acetylene is achieved even at residence times between 5 and 30 seconds. The preferred residence time is between 5 and 45 seconds.

The preferred temperature range is between 200° and 280° C. The higher the temperature is, the shorter can be the detention time for virtually the same transformations and yields.

The hydrofluorination of acetylene, in contrast to the known methods, does not have to be performed with an excess of hydrofluoric acid above the stoichiometrically required amount of two moles of HF per mole of acetylene. When the reactants are present in a stoichiometric ratio, the hydrofluorination becomes virtually complete. It is recommendable to use about a 10 percent excess of hydrofluoric acid, however. Basically, one can also use as much as a 50 percent excess of hydrofluoric acid.

The preparation of the catalyst is performed as follows:

Gamma or eta aluminum oxide which has preferably been heated at 80° C. for about 1 hour in a vacuum of less than 1 Torr, is imbibed with the aqueous solution of a bismuth salt and a manganese salt. Suitable bismuth salts are water-soluble or acid-soluble bismuth salts, in solutions which have been stabilized, if desired, with a complex forming agent. This complexing agent permits the preparation of a uniform solution of bismuth salts and also manganese salts of difficult solubility. Suitable complexing agents are, for example, hydroxyl-group-containing organic compounds from the group of the sugar alcohols, such as mannitol, sorbitol or ribitol, for example, or hydroxy acids such as tartaric acid, lactic acid or the sugar acids. Amines and nitriles are also suitable as complexing agents, examples being ethylenediamine, nitrilotriacetic acid or succinodinitrile.

A uniform solution can also be obtained by establishing a suitable acid pH, e.g. 0 to 4.

For the manganese compound, preference is given to the salt with the same anion as the bismuth salt that is used. However, any other water-soluble or acid-soluble manganese salt can be used as long as it does not form an insoluble precipitate with the bismuth salt under the specified conditions.

The manganese (II) and bismuth salts or bismuth oxy salts of nitric acid, sulfuric acid, hydrochloric acid or perchloric acid are used preferentially.

The concentration of the solution of the bismuth and manganese salts is not important, and is adapted to the desired metal content of the catalyst.

The aluminum oxide imbibed with the bismuth and manganese salt solution is then dried at temperatures up to 100° C., and then it is heated in a nitrogen atmosphere at 150° to 250° C. After the catalyst has been fully dried, the nitrogen is replaced with air and increasing concentrations of hydrogen fluoride. The exothermic reaction that then takes place is also performed at temperatures between 150° and 250° C. Towards the end of the exothermic reaction, the catalyst is heated in a 100% hydrogen fluoride atmosphere until the exothermic reaction dies out.

For the performance of the hydrofluorination reaction, acetylene is mixed with the above-stated excess of hydrogen fluoride and heated to the required reaction temperature. The preheated mixture is passed over the catalyst maintained at a constant temperature between 150° and 350° C. The catalyst in this case can be either in solid-bed form or in fluidized-bed form.

After passing through the catalyst, the gas mixture is washed and dried in a known manner.

The regeneration of the catalyst is accomplished by passing air through it at elevated temperatures, the temperatures required being only between 250° and 300° C., so that they are considerably lower than in the case of other processes for the regeneration of known catalysts. After such regeneration the catalyst again has a bright appearance and can be used for the hydrofluorination of acetylene with the same success as a freshly prepared catalyst. The regeneration described can be performed repeatedly without loss of catalyst activity.

The 1,1-difluoroethane obtained by the present method is an important intermediate for the preparation of vinylidene fluoride or of fluorinated hydrocarbons for use as refrigerants.

In order to more fully illustrate the nature of the invention and the manner of practicing the same, the following examples are presented.

EXAMPLES

Example 1

To prepare the catalyst, 700 grams of gamma aluminum oxide in pellets of 3 mm diameter are heated at 80° C. in a glass tube equipped with a heating jacket, for one hour at a vacuum of less than 1 Torr. Then it is cooled under vacuum to room temperature, and a solution of 160 grams of $Bi(NO_3)_3 \cdot 5H_2O$, 65 grams of $Mn(NO_3)_2 \cdot 4H_2O$ and 80 milliliters of 14N nitric acid in 900 ml of water is poured into the tube. After the imbibing mixture has been exposed to air by relieving the vacuum, it is let stand for one hour at 80° C. Then the aqueous phase is withdrawn and the catalyst mass is given a preliminary drying in a vacuum produced by a water-jet pump.

For hydrofluorination, the catalyst is poured into a double-jacketed nickel tube 150 cm long and 5 cm in diameter, whose temperature can be regulated by circulating oil. At 200° C. the catalyst is thoroughly dried with nitrogen and then activated with a mixture of air and an increasing concentration of hydrogen fluoride. The temperature is kept always below 250° C. by varying the hydrogen fluoride concentration. When a flow of 100 percent HF is reached, the treatment is continued for one more hour, and then the catalyst is dried with air for one hour. The fluoride content of the catalyst then amounts to about 50 percent, the bismuth content to about 5 percent and the manganese content to about 3 percent.

Through the catalyst prepared in this manner, a gaseous mixture, preheated to 80° C., of 1 volume-part of acetylene and 2 volume-parts of hydrogen fluoride is passed, with a residence time of 40 seconds. The temperature along the catalyst is between 200° and 220° C.

After washing and drying the reaction product contains:

96.5 percent $CH_3$—$CHF_2$
3.3 percent $CH_2$=$CHF$
0.2 percent $CH$≡$CH$

Example 2

A gaseous mixture of one volume-part of acetylene and 2.1 volume-parts of hydrogen fluoride, preheated to about 100° C., is passed through a catalyst prepared in accordance with Example 1, at 240° to 260° C. The residence time amounts to 28 seconds. The washed and dried reaction product consists of 97.5 percent $CH_3CHF_2$, 2.5 percent $CH_2$=$CHF$ and 0.1 percent $CH$≡$CH$.

The disclosure of DOS 2,000,200 is hereby specifically incorporated herein by reference.

What is claimed is:

1. A process for preparing 1,1-difluoroethane which comprises contacting acetylene with an agent consisting essentially of hydrogen fluoride in the presence of a catalyst consisting essentially of an aluminum fluoride containing catalyst at a temperature between 150° and 250° C. employing a residence time of 1 to 60 seconds, said catalyst being one prepared by imbibing gamma or eta aluminim oxide with a solution of a bismuth salt and a manganese salt, then heating the so-imbibed aluminum oxide at a temperature between 150° and 250° C., initially in a nitrogen atmosphere and then, after complete drying, in a mixture of hydrogen fluoride and increasing the concentration of hydrogen fluoride up to a 100 percent hydrogen fluoride atmosphere, said finished catalyst consisting essentially of:

0.1 to 20 weight percent of bismuth,
0.1 to 10 weight percent of manganese,
20 to 38 weight percent of aluminum,
32 to 60 weight percent of fluorine, any balance consisting essentially of oxygen.

2. A process according to claim 1 wherein the gamma or eta aluminum oxide which is imbibed is initially heated in a vacuum of approximately 1 Torr or less at a temperature between 50° and 120° C.

3. A process according to claim 1 wherein the acetylene and hydrogen fluoride are reacted in a molar ratio of 1 : 2 – 2.5.

* * * * *